United States Patent [19]

Dessau

[11] Patent Number: 5,103,066
[45] Date of Patent: Apr. 7, 1992

[54] DEHYDROGENATION OF ALCOHOLS OVER NON-ACIDIC METAL-ZEOLITE CATALYSTS

[75] Inventor: Ralph M. Dessau, Edison, N.J.

[73] Assignee: Mobil Oil Corp., Fairfax, Va.

[21] Appl. No.: 624,824

[22] Filed: Dec. 10, 1990

[51] Int. Cl.$^5$ .............................................. C07C 45/00
[52] U.S. Cl. ...................................... 568/406; 568/361; 568/322; 568/489
[58] Field of Search ............... 568/403, 404, 406, 485, 568/489, 361, 322

[56] References Cited

U.S. PATENT DOCUMENTS

| | | | |
|---|---|---|---|
| Re. 29,948 | 3/1979 | Dwyer et al. | 208/110 |
| 2,835,706 | 5/1958 | Cordes | 568/403 |
| 2,861,106 | 11/1958 | Opitz et al. | 568/403 |
| 3,013,990 | 12/1961 | Breck et al. | 568/403 |
| 3,702,293 | 11/1972 | Hayes et al. | 208/139 |
| 3,702,294 | 11/1972 | Rausch | 208/139 |
| 3,778,477 | 12/1973 | Mueller et al. | 568/403 |
| 3,878,131 | 4/1972 | Hayes | 252/466 PT |
| 3,981,923 | 9/1976 | Stouthamer et al. | 568/406 |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,560,804 | 12/1985 | Yeh et al. | 568/403 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,822,942 | 4/1989 | Dessau et al. | 585/419 |
| 4,830,729 | 5/1989 | Dessau et al. | 208/89 |
| 4,849,567 | 7/1989 | Dessau et al. | 585/379 |
| 4,851,599 | 7/1989 | Dessau | 585/407 |
| 4,868,145 | 9/1989 | Dessau et al. | 502/66 |
| 4,882,040 | 11/1989 | Dessau et al. | 208/138 |
| 4,886,926 | 12/1989 | Dessau et al. | 585/444 |
| 4,892,645 | 1/1990 | Dessau | 208/111 |
| 4,910,357 | 3/1990 | Dessau et al. | 585/322 |
| 4,931,416 | 6/1990 | Dessau et al. | 502/74 |
| 4,935,566 | 6/1990 | Dessau et al. | 208/65 |

FOREIGN PATENT DOCUMENTS

| | | | |
|---|---|---|---|
| 74651 | 9/1982 | European Pat. Off. | |
| 0107389 | 4/1984 | European Pat. Off. | |
| 2520636 | 1/1983 | France | |
| 823514 | 4/1958 | United Kingdom | 568/405 |
| 2033358 | 5/1980 | United Kingdom | |
| 2116450 | 1/1983 | United Kingdom | |

OTHER PUBLICATIONS

G. Wengui et al, "IR Study of Framework Vibrations and Surface Properties of High Silica Zeolites", Zeolites, Elsevir Science, Amsterdam, 1985, pp. 279-285.

Ione, Journal of Molecular Catalysis, 31, pp. 355-370 (1985).

Ione, "Structure and Reactivity of Modified Zeolites", Elsevir Science (1984), pp. 151-155.

Huagong, vol. 15, No. 7 (1986) (with translation).

*Primary Examiner*—James H. Reamer
*Attorney, Agent, or Firm*—Alexander J. McKillop; Charles J. Speciale; Marina V. Schneller

[57] ABSTRACT

The invention relates to a catalytic dehydrogenation of alcohols to produce ketones and/or aldehydes. The catalyst comprises a dehydrogenation metal and a non-acidic microporous crystalline material as a support. The support may contain indium, tin, thallium or lead, when the dehydrogenation metal is a Group VIII metal.

16 Claims, No Drawings

DEHYDROGENATION OF ALCOHOLS OVER NON-ACIDIC METAL-ZEOLITE CATALYSTS

FIELD OF THE INVENTION

The invention relates to the catalytic dehydrogenation of alcohols, including both primary and secondary alcohols. The catalyst for the dehydrogenation comprises a dehydrogenation metal and a non-acidic microporous crystalline support therefor. Dehydrogenation of primary alcohols will produce aldehydes while dehydrogenation of secondary alcohols will produce ketones.

BACKGROUND OF THE INVENTION

Dehydrogenation of alcohols is a commercially significant route in the production of aldehydes and ketones. Cf. Kirk-Othmer, ENCYCLOPEDIA OF CHEMICAL TECHNOLOGY, Vol. 1, pp. 105 and 183, and Vol. 13, page 905, Wiley-Interscience, Third Edition. Commercial processes for the production of acetone include the dehydrogenation of isopropanol; commercial processes for the production of methylethylketone include the dehydrogenation of 2-butanol. Frequent catalyst regeneration may be required due to build up of coke deposits. Cf. Kirk-Othmer, ENCYCLOPEDIA OF CHEMICAL TECHNOLOGY, p 183, Wiley-Interscience, Third Edition.

Crystalline microporous materials containing a modifier are described. The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material.

The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimension of 0.1 micron):

1 Small pore: n-$C_6$/i-$C_6$ sorption ratio greater than approximately 10.

2. Medium pore: n-$C_6$/i-$C_6$ is less than 10 and n-$C_6$/Mesitylene sorption ratio greater than approximately 5.

3. Large pore: n-$C_6$/Mesitylene sorption ratio less than approximately 5.

In the art, zeolites are a subclass of crystalline microporous silicates. Zeolites can contain aluminum as well as silicon. In some zeolites, the upper limit of the silicon/aluminum atomic ratio is unbounded. ZSM-5 is one such example wherein the silicon/aluminum atomic ratio is at least 2.5 and up to infinity. By way of illustration, U.S. Pat. No. 3,941,871, reissued as U.S. Pat. No. 29,948, discloses a porous crystalline silicate made from a reaction mixture containing no deliberately added aluminum and exhibiting the X-ray diffraction pattern characteristic of ZSM-5 zeolites; in certain examples tin is deliberately added to the silicate synthesis mixture.

Zeolites can be acidic or non-acidic, depending on the framework aluminum content and on the amount of compensating cations, such as $Na^+$, $K^+$, etc. ALPOs described in U.S. Pat. No. 4,310,440, which is incorporated by reference herein, are neutral. SAPOs described for example in U.S. Pat. No. 4,440,871, which is incorporated by reference herein, can be acidic or non-acidic depending on the ratio of framework Al:P therein and the compensating cation, such as $Na^+$, $K^+$ (other than proton species and other than proton forming species such as $NH^+_4$) ELAPOs are described in U.S. Pat. No. 4,500,651, while MeAPOs are described in U.S. Pat. Nos 4,544,143 and 4,567,029, each of said latter patents being incorporated by reference herein.

SUMMARY OF THE INVENTION

The invention relates to the dehydrogenation of alcohols to produce the corresponding ketones and aldehydes, in a catalytic process catalyzed by a non-acidic catalyst.

DETAILED DESCRIPTION OF THE INVENTION

In accordance with the invention, alcohols are dehydrogenated in the presence of a non-acidic catalyst. Production of ketones requires an alcohol which contains at least 3 carbon atoms. The alcohol can contain up to 30 carbon atoms or more; the exact number of carbon atoms of the reactant alcohol is not a critical parameter to the operation of the process. The hydrocarbon moiety of the alcohol can be aliphatic, alkyl, alkenyl or cycloaliphatic (preferably monocyclic cycloaliphatic, such as cyclohexanol) or aromatic (such as a monocyclic aromatic exemplified by benzyl alcohol). Examples of reactant alcohols include methanol, ethanol, 1-propanol, 2-propanol, 1-butanol, 2-butanol, 1-pentanol, 2-pentanol, and 3-pentanol, isoamyl alcohol, caprylic, caproic, palmitic, and stearic alcohols. Primary alcohols are necessary for production of aldehydes, by dehydrogenation. Dehydrogenation of secondary alcohols in accordance with the invention will produce ketones. Two examples of such alcohols which are of prime commercial interest include isopropanol and 2-butanol, because of the valuable products acetone and methyl ethylketone which are produced therefrom on dehydrogenation.

The conditions of dehydrogenation include a temperature ranging from about 100° to 500° C. and a pressure ranging from about 14 psia, or less, to about 300 psia. Hydrogen may be optionally cofed to the reaction zone in $H_2$/alcohol molar ratios of 0 to 10.0.

The catalysts employed in accordance with the invention comprise a dehydrogenation metal in combination with a non-acidic microporous crystalline support.

The dehydrogenation metal can comprise from 0.05 to 20 weight percent of the catalyst composition; preferably the dehydrogenation metal comprises from 0.1 to about 10 weight percent of the catalyst composition. The dehydrogenation metal can be any conventional dehydrogenation metal used in the art. The dehydrogenation metal can be any Group VIII metal, preferably platinum and copper, zinc, chromium, iron and gallium. Preferably the dehydrogenation metal is a platinum group metal. In embodiments described below, the dehydrogenation metal is platinum.

The non-acidic microporous crystalline support can contain at least one Group VIII metal modifier selected from the group consisting of indium, tin, thallium or lead with a content of the indium, tin, thallium or lead which can range from 0.01 to 20 weight percent of the crystalline microporous materials. Practically, the indium, tin, thallium or lead content will range from 0.1 to 10 weight percent of the microporous crystalline material.

The crystalline microporous materials are characterized by Si/Al ratios of at least 2. However, the silica:alumina ratio can be up to 1000 or even greater. In specific embodiments, the aluminum content of some of these materials is less than 0.1 weight percent, preferably less than 0.02 weight percent. In a preferred embodiment the microporous crystalline material is non-acidic, in the sense that it contains no framework aluminum, in the as-synthesized form.

Compositions used as catalysts in accordance with the invention do not exhibit any appreciable acid activity. These catalysts will meet the criteria of non-acidic catalysts described by Davis and Venuto, J. CATAL., Vol. 15, page 363 (1969). Alternatively, the non-acidic compositions will exhibit a pH of at least six when added to distilled deionized pH 7 water maintained under inert (such as argon) atmosphere; by an inert atmosphere in this context it means an atmosphere free of $CO_2$. Typically in these tests 100 mg of catalysts is added to 30 ml. of distilled deionized water. Some compositions will exhibit a pH of at least 7.5. Alternatively, the alkali metal content of these non-acidic materials exceeds the ion exchange capacity of the material of zeolite structure at a pH of 5 or less.

The microporous crystalline materials, if acidic as a result of synthesis, can be rendered non-acidic by base exchange to remove acidic functions contained therein. For example, if the microporous crystalline material contains framework aluminum, in the as-synthesized form, the microporous crystalline material can be base exchanged or impregnated. In this embodiment, base exchange or impregnation is effected after dehydrogenation metal incorporation. Base exchange can be with an ionic Group IA metal. The base-exchange can be accomplished by slurrying the material in an aqueous solution of suitable Group IA compound such as sodium hydroxide, potassium chloride, cesium hydroxide and the like. The base exchange can be accomplished under selected conditions of reagent concentration, pH, contact time, and the like, so as to eliminate substantially the base-exchangeable acidic content.

The non-acidic support component of the catalyst used in accordance with the invention is crystalline microporous material, such as the zeolites, ALPOs or SAPOs. Non-acidic zeolite supports include microporous crystalline materials containing silicon and optionally aluminum. The acidity (or non-acidity) of zeolites can depend on the framework aluminum content and/or on the amount of compensating cations, such as $Na^+$, $K^+$, $Cs^+$, etc. Decreasing acidity of zeolites can be effected by decreasing framework aluminum content. Compensating cations, such as alkali metal cations, exchanged for acidic protons in zeolites also renders the zeolites non-acidic. The most preferred zeolites used in the process of the invention are those which have been synthesized to contain indium, tin, thallium or lead in addition to the framework silicon.

The most preferred catalyst compositions used in the process of the invention are those Group VIII dehydrogenation metal containing materials which have been synthesized to contain indium, tin, thallium or lead in addition to the framework silicon. These are described in U.S. Pat. Nos. 4,886,926, 4,931,416, and in 4,868,145, each of which is relied upon and incorporated by reference herein, as well as in allowed patent application Ser. No. 211,198 filed June 24, 1988 which is also relied upon and incorporated by reference herein.

The microporous crystalline materials can have the X-ray diffraction pattern which corresponds to a zeolite, SAPO, ALPO, etc. For example, indium compositions which can be used in accordance with the invention have been made, the crystal structure of which is that of ZSM-5, ZSM-11, ZSM-12, ZSM-23, ZSM-48, ZSM-50, zeolite beta, ZSM-20, SAPO-5 and ALPO-5. These are characterized by pore sizes up to about eight angstroms. The X-ray diffraction pattern and significant lines tables of these materials have been described in the U.S. patent literature. In a preferred embodiment the pore size of the microporous crystalline silicate materials containing tin or indium ranges from 5 to about 8 angstroms.

When, as in embodiments herein, the non-acidic support exhibits an X-ray diffraction pattern of a zeolite, at least some of the dehydrogenation metal may be intra zeolitic, that is, some of that metal is within the pore structure of the crystal although some of that metal can be on the surface of the crystal. A test for determining whether, for example, Pt is intra zeolite or extra zeolitic in the case of ZSM-5 is reported by R. M. Dessau, J. CATAL., Vol. 89, page 520 (1984). The test is based on the selective hydrogenation of olefins.

In a preferred embodiment the pore size of the microporous crystalline materials ranges from about 5 to about 8 Angstroms. Preferably, the silicates exhibit X-ray diffraction patterns of zeolites which are characterized by Constraint Index of 1 to 12, when in their acidic forms.

The method by which Constraint Index of acidic zeolites is determined is described fully in U.S. Pat. No. 4,016,218, incorporated herein by reference for details of the method. Constraint Index (CI) values for some typical zeolites including some which are suitable as catalysts in the process of this invention are:

|        | CI (at test temperature) |
|--------|--------------------------|
| ZSM-4  | 0.5 (316° C.)            |
| ZSM-5  | 6-8.3 (371° C.-316° C.)  |
| ZSM-11 | 5-8.7 (371° C.-316° C.)  |
| ZSM-12 | 2.3 (316° C.)            |
| ZSM-20 | 0.5 (371° C.)            |
| ZSM-22 | 7.3 (427° C.)            |
| ZSM-23 | 9.1 (427° C.)            |
| ZSM-34 | 50 (371° C.)             |
| ZSM-35 | 4.5 (454° C.)            |
| ZSM-48 | 3.5 (538° C.)            |
| ZSM-50 | 2.1 (427° C.)            |
| MCM-22 | 1.5 (454° C.)            |

-continued

| CI (at test temperature) | |
|---|---|
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the process of the present invention. The very nature of this parameter and the above-referenced procedure by which it is determined, however, admits of the possibility that a given zeolite can be tested under somewhat different conditions and thereby exhibit different Constraint Indices. Constraint Index appears to very somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g. temperature, as to establish more than one value for the Constraint Index of a particular zeolite. This explains the range of Constraint Indices for some zeolites, such as ZSM-5, ZSM-11 and Beta.

The following Examples will illustrate the invention.

EXAMPLES

EXAMPLE 1

The dehydrogenation of isopropanol to acetone was accomplished using a non-acidic Pt/Sn-ZSM-5 as a catalyst. This catalyst contained 0.53% Pt, 1.23% Sn, 0.56% Na, and less than 0.01% Al. The catalyst was prepared in accordance with the disclosure of allowed U.S. application Ser. No. 211,198, filed June 24, 1988 now U.S. Pat. No. 4,990,710 which is relied upon and incorporated by reference herein; Example 3 below is illustrative. The reaction was conducted at 300° C. and atmospheric pressure, with a 5.2 IPA WHSV and a $H_2$/IPA ratio of 1. Under these conditions, an 87% yield of acetone was obtained. By-products constituted just over 3 weight %. No significant aging was observed over a period of five days.

EXAMPLE 2

Dehydrogenation of 2-butanol was undertaken over the same catalyst and under the same conditions of temperature, pressure and WHSV of Example 1. The yield was 91% methylethylketone with less than 3% side products.

EXAMPLE 3

A tin containing ZSM-5 sample was synthesized by dissolving $Sn(II)SO_4$ in deionized water and then adding NaOH. To this was added tetrapropylammonium bromide. The mixture was transferred to a 300 ml stainless steel autoclave and a low aluminum content silica gel (SPEX Ind.) was added with stirring. The resulting hydrogel was reacted at 160° C. for 5 days with stirring (400 rpm) before quenching. The resulting crystalline product was processed in the usual manner by filtering, washing and drying. X-ray diffraction analysis of the product zeolite showed it to be 100% crystalline ZSM-5.

The as-synthesized tin silicate was calcined first in nitrogen and then in air at 530° C. The calcined materials were ion-exchanged with aqueous $Pt(NH_3)_4Cl_2$ at room temperature at a pH of 9; 11 mg per gram silicate was used. The platinum tetramine-containing silicate was then calcined in oxygen to 350° C. at 0.5° C./min. Analysis indicated that this composition contained 0.53% Pt, 1.23% Sn, 0.56% Na, and less than 0.01% Al.

What is claimed is:

1. A process for producing ketones and aldehydes by contacting an alcohol, with an alcohol dehydrogenation catalyst, under alcohol dehydrogenation conditions, wherein the catalyst comprises a platinum group metal and a non-acidic microporous crystalline support, wherein the microporous crystalline support exhibits an X-ray diffraction pattern of the structure of a zeolite and producing a product mixture comprising hydrogen and a dehydrogenation product of said alcohol, said dehydrogenation product having the same number of carbon atoms as said alcohol.

2. The process of claim 1, wherein the metal is platinum.

3. The process of claim 1, wherein the zeolite, in acidic form, is characterized by a Constraint Index of 1 to 12.

4. The process of claim 1, wherein the microporous crystalline material exhibits the X-ray diffraction pattern of ZSM-5, ZSM-11, ZSM-12, ZSM-22, ZSM-23, ZSM-35, ZSM-48 and ZSM-50.

5. The process of claim 1, wherein the microporous crystalline material exhibits the X-ray diffraction pattern of ZSM-5 or ZSM-11.

6. The process of claim 1, wherein the support contains indium, thallium, lead or tin.

7. The process of claim 10, wherein the metal is platinum.

8. The process of claim 1, wherein the alcohol is aliphatic or aromatic.

9. The process of claim 1, wherein the alcohol is isopropanol.

10. The process of claim 1, wherein the alcohol is 2-butanol.

11. The process of claim 1, wherein the conditions include a temperature ranging from about 100° to 500° C.; a pressure ranging from about 14 psia to about 300 psia; and a hydrogen:alcohol molar ratio of 0 to 10.0.

12. The process of claim 1, wherein the support contains indium, thallium, lead or tin, in an amount ranging from 0.01 to 10 weight percent.

13. The process of claim 1, wherein the catalyst comprises 0.1 to 10 weight percent of metal.

14. The process of claim 6, wherein the alcohol is aliphatic or aromatic.

15. The process of claim 6, wherein the alcohol is isopropanol.

16. The process of claim 6, wherein the alcohol is 2-butanol.

* * * * *